US00PP23567P3

(12) United States Plant Patent
Korlipara

(10) Patent No.: US PP23,567 P3
(45) Date of Patent: Apr. 23, 2013

(54) *GAILLARDIA* PLANT NAMED 'TNSF'

(50) Latin Name: *Gaillardia×grandiflora*
Varietal Denomination: TNSF

(75) Inventor: Harini Korlipara, Canby, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 92 days.

(21) Appl. No.: 13/200,257

(22) Filed: Sep. 21, 2011

(65) Prior Publication Data

US 2013/0074238 P1 Mar. 21, 2013

(51) Int. Cl.
*A01H 5/00* (2006.01)

(52) U.S. Cl.
USPC ..... Plt./431

(58) Field of Classification Search ..... Plt./431
See application file for complete search history.

*Primary Examiner* — June Hwu

(74) *Attorney, Agent, or Firm* — Klarquist Sparkman, LLP

(57) ABSTRACT

A new and distinct *Gaillardia* plant named 'TNSF' characterized by a very compact habit, tubular ray florets of yellow orange with dark red bases, and excellent vigor.

1 Drawing Sheet

Botanical denomination: *Gaillardia×grandiflora.*
Variety designation: 'TNSF'.

BACKGROUND OF THE INVENTION

The present invention relates to a new and distinct cultivar of *Gaillardia×grandiflora* and given the cultivar name 'TNSF'. *Gaillardia* is in the family Asteraceae. This new cultivar is a third generation seeding originating from a planned breeding program to create new dwarf *Gaillardia.* The exact parents are unknown, unreleased, proprietary plants.

Compared to *Gaillardia* 'Fanfare' (U.S. Plant Pat. No. 15,892), the new cultivar is more compact and the ray floret color with more yellow orange.

Compared to *Gaillardia* 'Frenzy' (U.S. Plant Pat. No. 19,943), the new cultivar is more compact and the ray florets are much more yellow orange in color.

Compared to *Gaillardia* 'Sun Devil' (U.S. Plant patent applied for concurrently), the new cultivar has larger inflorescences with ray florets with longer, more prominent tubes and much more yellow orange color.

SUMMARY OF THE INVENTION

This new *Gaillardia* cultivar is distinguished by:

1. a very compact habit,
2. tubular ray florets of yellow orange with dark red bases, and
3. excellent vigor.

This new cultivar has been reproduced only by asexual propagation (division and tissue culture). Each of the progeny exhibits identical characteristics to the original plant. Asexual propagation by division and tissue culture using standard micropropagation techniques with terminal and lateral shoots, as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE DRAWING

FIG. 1 shows *Gaillardia* 'TNSF' in full bloom as a 6 month old in a 1 gallon container grown in full sun in late July in Canby, Oreg.

DETAILED PLANT DESCRIPTION

The following is a detailed description of the new *Gaillardia* cultivar based on observations of 6-month-old specimens growing in one gallon containers outside in full sun in Canby, Oreg. Canby is in Zone 8 on the USDA Hardiness map. Temperatures range from a high of 95 degrees F. in August to an average of 32 degrees F. in January. Normal rainfall in Canby is 42.8 inches per year in the trial fields in Canby, Oreg. The color descriptions are all based on *The Royal Horticultural Society Colour Chart,* 5$^{th}$ edition.

Plant:

*Type.*—Herbaceous perennial.
*Hardiness.*—USDA Zones 3 to 9.
*Size.*—Grows to 30 cm wide and 25 cm tall to top of inflorescences.
*Form.*—Basal clump, with about 6 main stems from the base.
*Vigor.*—Excellent.
*Roots.*—Fibrous, with many downward growing and few laterals, ivory in color, Yellow White 158D, roots develop easily from stem cuttings.

Stem:

*Type.*—Ascending.
*Size.*—10 mm wide at the base and grows to about 8 cm long to flowering branches.
*Number of stems from the crown.*—About 6 main stems, each of these branch at every node.
*Internode length.*—5 to 10 mm.
*Surface.*—Pubescent.

*Color.*—Yellow Green 147C with tints of Greyed Purple 187A in sun.

Leaf:

*Type.*—Simple.

*Shape.*—Oblanceolate.

*Arrangement.*—Alternate.

*Size.*—Grows to 15 cm long and 2.7 cm wide.

*Margins.*—Entire.

*Venation.*—Pinnate.

*Apex.*—Acute.

*Surface texture.*—Pubescent on both sides.

*Petiole.*—Leaves more attenuate on basal leaves, no visible petiole.

*Color.*—Top and bottom sides Green N137A with main vein Yellow Green 145D.

Inflorescence:

*Type.*—Stalked terminal heads, daisy type.

*Peduncle.*—Grows to 11 cm long and 3 mm wide, pubescent, Greyed Green 191A.

*Size.*—Grow to 10 cm wide and 3 cm deep.

*Immature.*—2 cm deep and 3 cm wide, bowl-shaped with phyllaries and ray florets cupping upwards, ray florets tubular, pubescent, Greyed Orange 167A, disc 17 mm wide and Greyed Purple 187B on outer half, center Yellow Green 145A.

*Receptacle.*—Disc shaped, becoming 5 mm wide and 1.5 mm deep, Yellow Green 145D.

*Phyllary.*—About 38 in number, cupping upwards; grow to 17 mm long and 5 mm wide, lance-attenuate, margin entire, tip acuminate, pubescent and Green 137A on both sides.

*Disc.*—Conic, deeper with maturity, 35 mm wide and becoming 15 mm deep with maturity, Greyed Purple 187B.

*Lastingness.*—Each inflorescence 7 to 14 days on the plant.

Florets:

*Arrangement.*—Radiate.

*Ray florets.*—Grow to 40 mm long and 25 mm wide, about 21 in number with no pistil or stamen, pubescent outside and glabrous inside, tubular and three to four lobed; lobes oblong, unequal in width, 20 mm long and 5 to 6 mm wide, margins entire, with the tips notched; tube 28 mm long and 1 to 6 mm wide; back side color Greyed Purple 185A on bottom ½ of floret and into the veins toward the lobes to Yellow Orange 15A on top half, inside color Greyed Purple 187B on bottom and Yellow Orange 15A on top with a band of Orange Red N34A in the middle.

*Disc florets.*—With stamen and pistil, about 140 in number, 20 mm long and 3 mm wide, tubular; corolla 12 mm long and 3 mm wide, 5 lobed, pubescent outside and glabrous inside, Greyed Purple 187A on lobe tips to Red 53B on top ⅓ to Greyed Purple 185B on middle ⅓ to Yellow Green 145D on bottom ⅓; pistil 1, ovary 4 mm long, hairy, Yellow Green 145D, style 4 mm long, White 155A, with extruding 2-branched stigma, 5 mm long, Greyed Purple 187A; stamen 5, 7 mm long, Greyed Orange 165C, anthers 5 mm long, pollen Yellow Orange 15A.

*Bloom period.*—June through September in Canby, Oreg.

*Fragrance.*—Light, *Chrysanthemum*-like.

*Seed.*—None seen.

*Fertility.*—Infertile.

Disease and pests: Insect and disease resistance is believed to be typical for the genus.

I claim:

1. A new and distinct *Gaillardia* plant as herein illustrated and described.

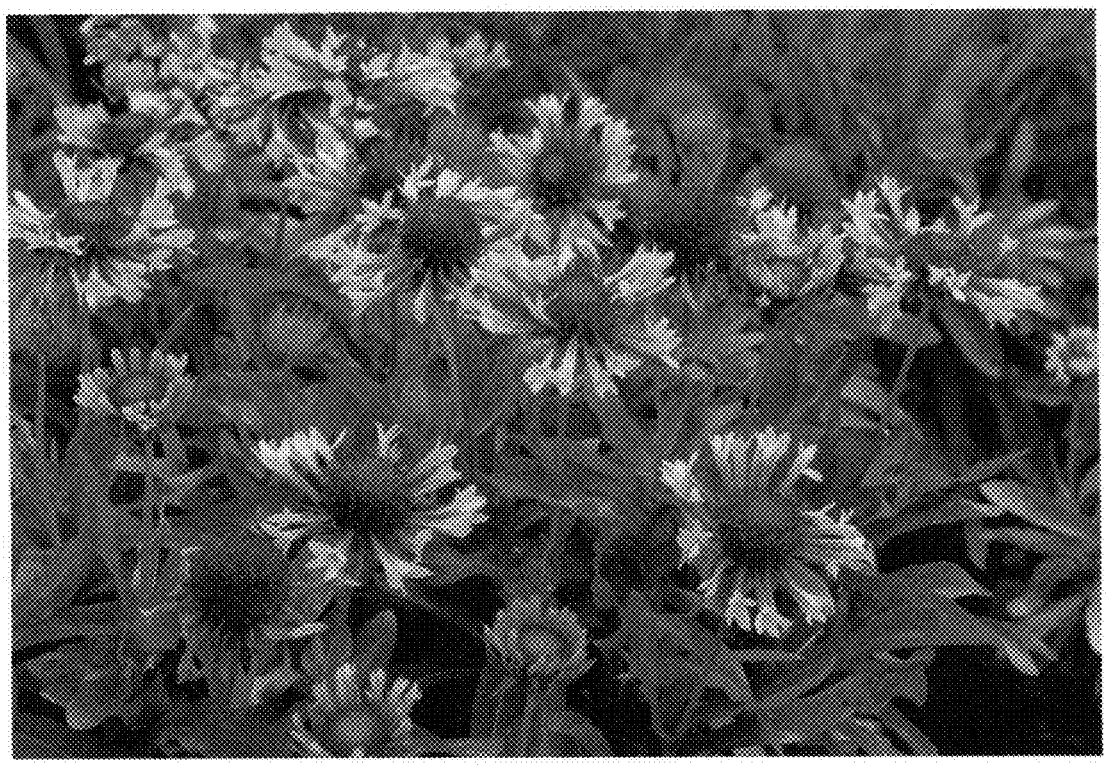

* * * * *